United States Patent [19]

Cavalli et al.

[11] Patent Number: 4,829,042

[45] Date of Patent: May 9, 1989

[54] CATALYST SUITABLE FOR THE OXIDATION OF METHYL ALCOHOL TO FORMALDEHYDE AND METHOD FOR PREPARING THE CATALYST

[75] Inventors: Luigi Cavalli; Mario Cucchetto, both of Novara; Guido Petrini, Galliate; Augusto Viola, Armeno, all of Italy

[73] Assignee: Ausimont S.p.A., Milan, Italy

[21] Appl. No.: 175,618

[22] Filed: Mar. 29, 1988

Related U.S. Application Data

[63] Continuation of Ser. No. 75,186, Jul. 15, 1987, abandoned, which is a continuation of Ser. No. 854,787, Apr. 23, 1986, abandoned.

[30] Foreign Application Priority Data

Apr. 24, 1985 [IT] Italy .................................. 20476 A/85

[51] Int. Cl.$^4$ .............................................. B01J 23/88
[52] U.S. Cl. ........................................ 2/316; 568/474
[58] Field of Search ......................... 502/316; 568/474

[56] References Cited

U.S. PATENT DOCUMENTS

| | | | |
|---|---|---|---|
| 2,812,308 | 11/1957 | Shelton et al. | 502/316 X |
| 3,152,997 | 10/1964 | Natta et al. | 502/316 |
| 3,408,309 | 10/1968 | Gessner | 502/316 |
| 3,846,341 | 11/1974 | Courty | 502/316 X |
| 3,978,136 | 8/1976 | Friedrich et al. | 568/474 |
| 4,331,567 | 5/1982 | Canavesi et al. | 502/316 X |

*Primary Examiner*—W. J. Shine
*Attorney, Agent, or Firm*—Stevens, Davis, Miller & Mosher

[57] ABSTRACT

Catalyst suitable for the oxidation of $CH_3OH$ to $CH_2O$, comprising a mixture of a well known catalytic system, herein indicated as mixed oxides, based on $FE_2(MoO_4)_3$ molybdenum trioxide ($MoO_3$) with non-sintered of $Fe_2O_3$ from 5 to 90% by weight of the sum of $Fe_2O_3$ + mixed oxides, the surface area of the $Fe_2O_3$ being from 1 to 10 m$^2$/g and the superficial area of the whole catalyst being from 1 to 6 m$^2$/g.

9 Claims, 1 Drawing Sheet

CATALYST SUITABLE FOR THE OXIDATION OF METHYL ALCOHOL TO FORMALDEHYDE AND METHOD FOR PREPARING THE CATALYST

BACKGROUND

This application is a continuation of application Ser. No. 075,186, filed July 15, 1987, which is a continuation of Application Ser. No. 854,787 filed Apr. 23, 1986, both now abandoned.

The oxidation of $CH_3OH$ to $CH_2O$, with $O_2$ or other gas containing oxygen, is usually carried out in the presence of catalysts based on Ag or ferro-molybdate; sometimes a combination of these two catalysts is used in two stages of a same plant. The highly exothermic oxidation with Fe-Mo catalysts is carried out in static bed and tube nest reactors, in which heat is removed indirectly by a thermic fluid. In the most common catalytic beds of the Mo/Fe type, air and $CH_3OH$ are fed, as well as streams of recycled gas, the content of $CH_3OH$ being between 6 and 9.5% by volume and the maximum temperature of the hot spots being between 300° and 430° C., while the average temperature should be from 240° to 400° C., and better still 270°–370° C. It is a good rule, moreover, to add an inert seal at the beginning and the end of the catalytic layer, as suggested in British Pat. No. 1,057,080. The Mo/Fe catalysts used up to now, hereinafter referred to as "mixed oxides", are prepared by coprecipitation from solutions of ferric and molybdic salts, and are made up of mixtures of ferromolybdate and Mo oxide, uncombined. These mixed oxides, in which molybdenum prevails over iron, do not, however, give completely satisfactory yields, especially when a double catalytic layer is used (see British Pat. No. 1,463,174), to better control the temperature and increase the selectivity of oxidation into $CH_2O$.

U.S. Pat. No. 2,812,308 owned by Reichold Company teaches the improved use of the combination of mixed oxides, with sintered ferric oxide or silicon carbide. With regard to the ferric oxide, the patent specifies that a sintered oxide must be used, sintering temperatures usually being from 1090° to 1370° C. (see Encyclopedia of Chemical Technology; Wiley-Interscience Publication Editor; Third Edition (1983) volume 21, page 94).

At these temperatures, however, the porosity of the oxides disappears and some chemical transformations take place. For instance, if ferric oxide is heated above the 800°–900° C. range, in which there is an equilibrium between $Fe_2O_3$ and magnetite, ferric oxide loses oxygen and is gradually converted into $Fe_3O_4$. Mixtures of "mixed oxides" with porous rhombohedral pulvrized ferric oxide, of the non-sintered type usually used as a pigment, having a surface area (B.E.T.) generally higher than 20 $m^2/g$, do not give satisfactory results.

We have unexpectedly found catalysts which are much more effective, based on mixtures of "mixed oxides" plus ferric oxides, which possess high mechanical resistance and thermal stability, as well as a very long life. The mechanical resistance, as known, eliminates the pressure losses due to catalyst crumbling (see U.S. Pat. No. 3,978,136). Another result we obtain is that of a much higher selectivity $CH_2O$, such a way that it is possible to use higher concentrations of $CH_3OH$ feed, thus obtaining higher final yields in $CH_2O$.

DESCRIPTION OF THE INVENTION

In its most general form, the present invention concerns a high yield, high resistance catalyst suitable for the oxidation of $CH_3OH$ to $CH_2O$ comprising the mixture of a particular known catalytic system, herein indicated as "mixed oxides", based on ferro-molybdate and Mo oxide, in which system, obtained through coprecipitation, the Mo/Fe molar ratio is from 1.8 to 5 and preferably from 2 to 4, with an amount of non-sintered ferric oxide, $Fe_2O_3$, not combined with Mo, having a surface area of from 1 to 10, preferably from 2 to 6 $m^2/g$ and preferably the feric oxide has a specific surface area not higher than 5 $m^2/g$ and more preferably not higher than 3 $m^2/g$, from 5 to 90% by weight, preferably from 10 to 70% and more preferably from 20 to 50% of the sum of $Fe_2O_3+$ mixed oxides, the surface area of the entire catalyst being from 1 to 6 $m^2/g$. It was surprisingly found that the introduction of a non-sintered ferric oxide having the above mentioned specific surface, not only is not the reason of substantial changes in the phase composition of the "mixed oxides", the oxide being little reactive in regard to the uncombined molybdenum trioxide, but also gives to the catalysts valued properties of mechanical resistance and yield, even for a very long time of use.

The new catalysts, in fact, possess exceptional mechanical resistance, up to 18 kg per pellet and more with reference to the bored pellet prepared according to Example 3 hereof, and very high yield, for very long periods, up to approximately 1 kg/h of $CH_2O$ per $dm^3$ of catalyst (apparent volume), said yield being independent of the activity and selectivity of the catalyst, as well as of the oxidation temperature. The Mo quantities necessary for the preparation of the catalyst are very reduced and this is a great advantage since molybdenum is a very expensive raw material. The selectivity of the new catalyst both with regard to formaldehyde and to the undesired by-products ($CO$ and $CO_2$), is practically independent of the temperature and that corresponds to high reactor stability; the importance of a constant selectivity is put well in evidence in the above-mentioned United States Patent. The greatest part of the excellent characteristics described above disappear, or are reduced, if the surface area of the non-sintered ferric oxide is too high or if it is practically reduced to zero.

These new catalysts can be prepared by different methods, the method described hereinbelow being only an example and in no way limiting.

A solution of a molybdic salt, for instance, ammonium dimolybdate $(NH_4)_2Mo_2O_7$ or ammonium paramolybdate having formula $(NH_4)_6Mo_7O_{24}\cdot4H_2O$, and a solution of ferric salt, for instance, hexahydrated ferric chloride or non-hydrated ferric nitrate, are mixed in such quantities as to obtain a molar ratio Mo/Fe from 1.8 to 5 in the final product. The addition of an acid, for instance HCl, suitably adjusting the pH, can accelerate the coprecipitation which brings about the formation of the mixed oxides, as described, for instance, in U.S. Pat. Nos. 3,408,309; 3,198,753 and 3,152,997. The water is then removed, for instance by siphoning, centrifugation or evaporation. Pulverized non-sintered $Fe_2O_3$, together with stearic acid, graphite or other conventional lubricant is added to the mixed oxides, which may be wet, dried, calcined, or, possibly, ground.

Excellent results are obtained, particularly with respect to extruded products, by also adding a cellulosic binder, such as hydroxypropyl cellulose, with the non-sintered $Fe_2O_3$. Preferably, the amount of the binder added with the $Fe_2O_3$ is from 0.5 to 5% by weight on the sum of $Fe_2O_3$ plus the mixed oxides. The powder or paste is then formed, for instance as cylinders, rings, balls, granules, saddles, extruded pellets, etc. The catalyst obtained is gradually heated in an oxidizing atmosphere, for an activation, from room temperature up to 300°–600° C., preferably 400°–550° C., in a time of approximately 12–36 hours, the final temperature being maintained for at least a further 4 hours. Before activation it is better to dry the extruded catalysts at 100°–120° C. The average diameter of the granules is generally from 3 to 5 mm.

BRIEF DESCRIPTION OF THE DRAWINGS

The invention is illustrated, in a non-limiting way, in the accompanying drawing, in which.

Figure 1:
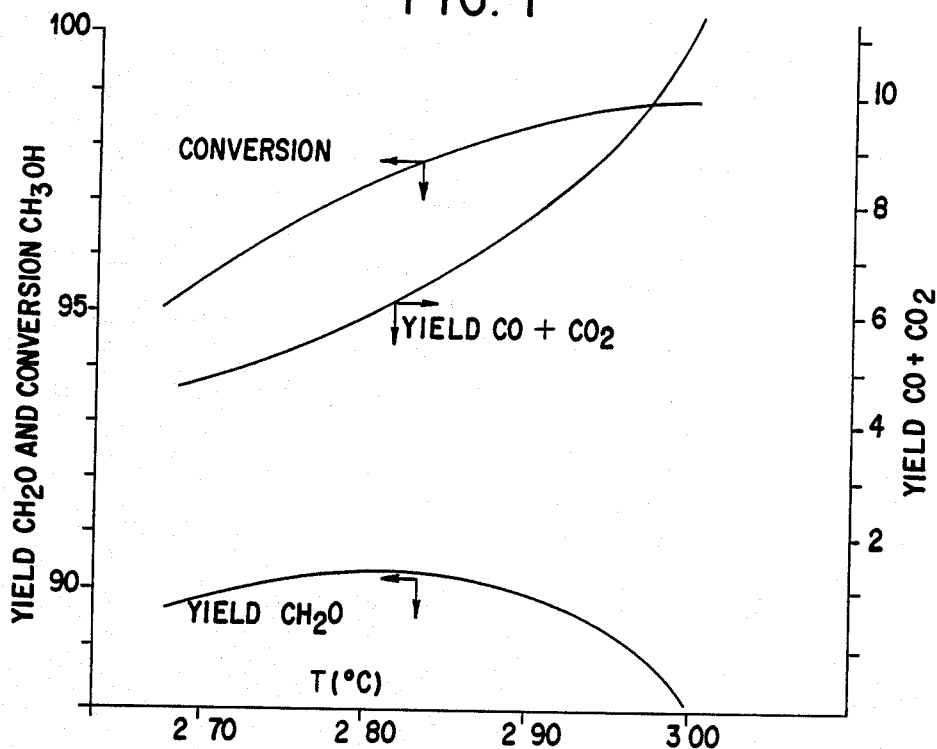
FIG. 1 shows the results obtained with catalysts formed only of mixed oxides, as in Example 2.
Figure 2:
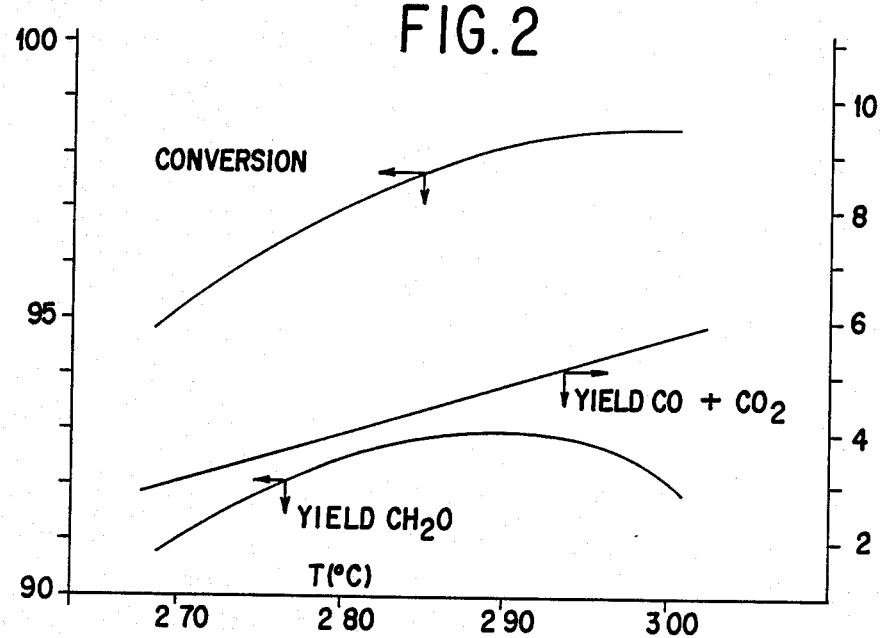
FIG. 2 shows the results obtained with catalysts containing 30% by weight of non-sintered $Fe_2O_3$, as in Example 4.

In obtaining the results shown in FIGS. 1 and 2, the operating conditions were maintained constant, except for the temperature which is considered as an independent variable.

According to a preferred embodiment, the Mo/Fe molar ratio in the "mixed oxide" system should be from 1.8:1 to 4:1 and the ferric oxide should have a surface area not higher than 5 and preferably not higher than 3 $m^2/g$; furthermore, the average size of the ferric oxide particle should not be lower than 0.2 mm and preferably now lower than from 0.2 to 1 mm.

The following examples are provided for illustrating the invention in more detail and are not intended to be limiting of the spirit and scope thereof.

EXAMPLE 1—PREPARATION OF THE "MIXED OXIDES"

To a solution, at pH=5.6, of 5 kg of ammonium dimolybdate, at 56% by weight of Mo, in 90 $dm^3$ of deionized $H_2O$, heated to 60° C., the following were added gradually over a period of 60 minutes: 3.15 kg of $FeCl_3 6H_2O$, at 20% by weight of Fe, dissolved in 50 $dm^3$ of deionized $H_2O$, at room temperature (pH of the chloride solution=1.4).

The dispersion was then diluted up to 180 $dm^3$ (pH of the diluted solution=1.7) and was left to decant until it was possible to siphon off 120 $dm^3$ of liquid; the Mo/Fe molar ratio was 2.58 in the reagents. It was washed 5 times by decantation, using approximately 120 $dm^3$ of deionized $H_2O$ each time. The product, wherein the Mo/Fe molar ratio was 2.53, was filtered and the precipitate was dried, first at 120° C. for 8 hours, and then at 190° C. for about 6 hours. The scales obtained were ground, reducing their dimension to under 1.5 mm, and the powder was added with stearic acid and at last tableted in,the form of bored cylinders (dimensions: 5×5 mm; bore diameter=2.5 mm), and in the case of bored shapes the average size thereof is equal to or larger than 4 mm. Activation was carried out in air by gradually heating from room temperature to 500° C., in 18 h, and maintaining the final temperature for 4 hours. The oven was then turned off and the product was extracted at below 100° C.

EXAMPLE 2 (COMPARATIVE) USE OF THE MIXED OXIDES

221 $cm^3$ (apparent volume) of the bored cylinders prepared according to Example 1 were loaded in a reactor having an internal diameter of 20.4 mm. The reactor was placed in a bath of molten salts and was then fed with a gaseous mixture containing 9% of $CH_3OH$, and 10.5% of $O_2$ (by volume), the rest being $N_2$, at a space velocity of 6,000 $h^{-1}$ (6,000 normal liters/h of gas per liter of apparent catalytic volume) with a temperature of the salts of 280° C. The conversion of methyl alcohol (see Table 1) was 97.3% and the $CH_2O$ yield was 90.5%.

EXAMPLE 3—PREPARATION OF $Fe_2O_3$ for MIXTURES 25 kg of pulverized ferric oxide, having a specific surface area of 2.7 $m^2/g$, were placed in a mixer and added with: 1.36 kg of stearic acid; 0.54 kg of hydroxypropyl cellulose; 0.27 kg of graphite. After dry mixing, 6.6 $dm^3$ of deionized water were added to the mass, and the mixing continued for 2 hours, after which the paste was dried for approximately 8 hours at 110°–115° C., cooled down, ground and screened. The granulometric fraction between 0.2 and 1 mm ($Fe_2O_3$ content=92% by weight) was used for the preparation of the catalyst of Example 4. In all the other examples the ferric oxide was used as such (in powder).

EXAMPLE 4

70 kg of mixed oxides, dried and ground, as in Example 1, were intimately mixed with 32.6 kg of non-sintered $Fe_2O_3$, prepared according to Example 3. The mixture was added with the lubricant, tableted to obtain cylinders as in Example 1, and activated as in Example 1. Afterwards, 221 $cm^3$ of catalyst were loaded in the reactor of Example 2 and tested in the same operating conditions. The $CH_2O$ yield (see Table 1) was 92.5%.

EXAMPLE 5

The catalyst of Example 4 was tested in slightly different conditions; data and results are shown in Table 1.

EXAMPLE 6

50 kg of mixed oxides, prepared, dried and ground according to Example 1, were intimately mixed with 50 kg of non-sintered $Fe_2O_3$ in powder, the lubricant was added, and the mass tableted to obtain bored cylinders (dimensions: 4×4 mm; bore=2 mm), and activated according to Example 1. The resulting cylinders (229 $cm^3$) were loaded in the reactor of Example 2. Data and results are shown in Table 1.

EXAMPLE 7

Example 6 was repeated, slightly varying $Fe_2O_3$/mixed oxides ratio. Data and results (totally satisfying) are shown in Table 1.

EXAMPLE 8 (COMPARATIVE)

A catalyst in the form of 4×4 mm bored cylinders having a bore of 2 mm, prepared and activated according to Example 1, i.e., omitting the addition of non-sintered $Fe_2O_3$, was loaded in the reactor of Example 2. Data and results are shown in Table 1.

EXAMPLE 9

Example 6 was repeated, modifying the Fe$_2$O$_3$/mixed oxides ratio as well as the operating conditions. Data and results are shown in Table 1.

EXAMPLE 10

50 kg of mixed oxides prepared according to Example 1, dried to 120° C. and ground below 0.5 mm, were intimately mixed with 50 kg of non-sintered Fe$_2$O$_3$ in powder, added with 1 kg of hydroxypropyl cellulose as binder, and mixed with water and extruded in solid cylinders (approximate dimensions: 4×4 mm). The cylinders were dried at 100°–110° C. for a night and then activated according to Example 1. Data and results are shown in Table 1.

EXAMPLE 11

30 kg of mixed oxides prepared according to Example 1, dried to 120° C. and powdered below 0.5 mm were intimately mixed with 70 kg of Fe$_2$O$_3$ in powder, additioned with 1 kg of hydroxypropyl cellulose and then mixed with water and extruded in solid cylinders (approximate dimensions: 4×4 mm). The cylinders were dried at 100°–110° C. overnight and activated according to Example 1. Data and results are shown in Table 1.

TABLE

| EXAMPLE | 2 (a) | 4 | 5 | 6 (b) | 7 (b) | 8 (a) & (b) | 9 (b) | 10 (c) | 11 (c) |
|---|---|---|---|---|---|---|---|---|---|
| "Mixed Oxides" (kg) | — | 70 | 70 | 50 | 60 | — | 70 | 50 | 30 |
| non-sintered Fe$_2$O$_3$ (kg) | 0 | 30 | 30 | 50 | 40 | 0 | 30 | 50 | 70 |
| Apparent Volume (cm$^3$) | 221 | 221 | 221 | 229 | 229 | 229 | 229 | 221 | 221 |
| SV (h$^{-1}$) | 6,000 | 6,000 | 6,000 | 8,200 | 8,200 | 8,000 | 8,000 | 6,000 | 6,000 |
| Bath Temperature (°C.) | 280 | 280 | 290 | 280 | 280 | 260 | 270 | 290 | 300 |
| CH$_3$OH (% Vol.) | 9. | 9. | 6. | 6. | 6. | 9. | 9. | 9. | 9. |
| O$_2$ (% Vol.) | 10.5 | 10.5 | 10.5 | 11.5 | 11.5 | 9.5 | 9.5 | 10.5 | 10.5 |
| RESULTS (%): | | | | | | | | | |
| Conversion CH$_3$OH | 97.3 | — | — | — | — | — | 98.4 | — | — |
| Selectivity CH$_2$O | 93.0 | — | — | — | — | — | 94.6 | — | — |
| Yield (d) | 90.5 | 92.5 | 93.7 | 93.8 | 94.6 | 91.2 | 93.1 | 93.05 | 92.20 |
| Resistance (kg) (e) | 14. | 18. | 18. | — | — | — | — | — | — |

(a) Comparative;
(b) Bored Cylinders 4 × 4 mm (Diameter of the Bore = 2 mm);
(c) Solid Extruded Cylinders;
(d) Yield = Conversion × Selectivity: 100 (percentages are molar);
(e) Mechanical Resistance to Compression of a Single Granule

We claim:

1. A high yield catalyst having high mechanical resistance, for the oxidation of methanol to formaldehyde, comprising a specific catalytic system referred to as mixed oxides, based on iron-molybdate and molybdenum trioxide, said system being obtained through co-precipitation, the Mo/Fe molar ratio is from 1.8:1 to 5:1, and is characterized in that said mixed oxides are used in admixture with an amount of non-sintered ferric oxide from 5 to 90% by weight of the sum Fe$_2$O$_3$+ mixed oxides, the surface area of said Fe$_2$O$_3$ being from 1 to 10 m$^2$/g and the surface area of the catalyst, as a whole, being from 1 to 6 m$^2$/g.

2. A catalyst according to claim 1, wherein the Mo/Fe molar ratio in the mixed oxides is from 1.8:1 to 4:1, and wherein the amount of Fe$_2$O$_3$ is from 10 to 70% by weight with respect to the sum of Fe$_2$O$_3$+ mixed oxides.

3. A catalyst according to claim 1, wherein the Mo/Fe molar ratio in the mixed oxides is from 2:1 to 4:1 and wherein the amount of Fe$_2$O$_3$ is from 20 to 50% with respect to the sum Fe$_2$O$_3$+ mixed oxides.

4. A catalyst according to claim 1, wherein the surface area of said Fe$_2$O$_3$ is not higher than 5 m$^2$/g.

5. A catalyst according to claim 1, wherein the suface area of said Fe$_2$O$_3$ is not higher than 3 m$^2$/g.

6. A catalyst according to claim 1 in the form of bored cylinders having an average size equal to or larger than 4 mm.

7. A method for the preparation of the catalyst according to claim 1, wherein said mixed oxides and said non-sintered ferric oxide are mechanically blended in the presence of an adjuvant selected from the group consisting of lubricants and binders.

8. The method according to claim 7, wherein said binder is hydroxypropyl cellulose and wherein the amount of hydroxypropyl cellulose is from 0.5 to 5% by weight with respect to the sum Fe$_2$O$_3$+ mixed oxides.

9. A method according to claim 7, wherein the non-sintered ferric oxide is in the form of agglomerated particles having an average size not lower than 0.2 mm.

* * * * *